United States Patent [19]

Kurkov

[11] 4,382,948

[45] May 10, 1983

[54] 1,3,4-TRISUBSTITUTED-2-PYRAZOLIN-5-ONE FUNGICIDES

[75] Inventor: Victor P. Kurkov, San Rafael, Calif.

[73] Assignee: Chevron Research Company, San Francisco, Calif.

[21] Appl. No.: 361,653

[22] Filed: Mar. 25, 1982

[51] Int. Cl.$^3$ .................... A01N 43/56; C07D 231/20
[52] U.S. Cl. ............................... 424/273 P; 548/365; 542/442
[58] Field of Search ............... 548/365, 362, 363, 367; 424/273 P

[56] References Cited

FOREIGN PATENT DOCUMENTS 2513750  10/1975  Fed. Rep. of Germany .

OTHER PUBLICATIONS

Dhal et al., Chem. Abst., 1976, vol. 85, No. 5544v.
Suman et al., Chem. Abst., 1981, vol. 94, No. 65535p.

*Primary Examiner*—John M. Ford
*Assistant Examiner*—Natalia Harkaway
*Attorney, Agent, or Firm*—D. A. Newell; T. G. De Jonghe; L. S. Squires

[57] ABSTRACT

Novel 1,3,4-trisubstituted-2-pyrazolin-5-ones of this invention are excellent fungicides, especially against rice blast.

11 Claims, No Drawings

1,3,4-TRISUBSTITUTED-2-PYRAZOLIN-5-ONE FUNGICIDES

BACKGROUND OF THE INVENTION

This invention pertains to novel fungicides. With the world more dependent for food on an ever decreasing amount of cultivated land, it is necessary to develop fungicides which protect crops from fungicidal destruction.

GP No. 2,513,750 discloses 1,3,4-trisubstituted pyrazoles as herbicides.

SUMMARY OF THE INVENTION

The compounds of the present invention are represented by the formula:

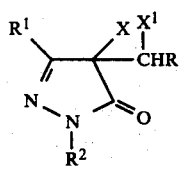

wherein R is phenyl or phenyl substituted with 1 to 3 substituents independently selected from fluoro, chloro, bromo, iodo, nitro, and trifluoromethyl; $R^1$ is lower alkyl; $R^2$ is lower alkyl; and X and $X^1$ are independently halogen.

Preferred R groups include for instance, 2,4-dihalophenyl, 3,4-dihalophenyl, 4-halophenyl and 2,6-dihalophenyl. Due to its superior fungicidal activity, a particularly preferred R group is 2,4-dihalophenyl. Most preferably R is 2,4-dichlorophenyl.

Preferred $R^1$ groups include for instance, methyl, ethyl, n-propyl and isopropyl. Particularly preferred compounds of this invention are those wherein $R^1$ is methyl.

Preferred $R^2$ groups include, for instance, methyl, ethyl, n-propyl, isopropyl and n-hexyl. A particularly preferred $R^2$ group is methyl.

Preferred X and $X^1$ halogens are chloro and bromo. Particularly preferred X and $X^1$ halogens are chloro.

Among other factors, the present invention is based on my finding that the compounds of this invention are surprisingly effective fungicides. In particular, the compounds disclosed herein are especially effective against Rice Blast.

DEFINITIONS

As used herein the following terms have the following meanings, unless expressly stated to the contrary.

The term "alkyl" refers to both straight- and branched-chain alkyl groups. The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl and the like.

The term "halo" or "halogen atom" refers to the groups fluoro, chloro, bromo and iodo.

The term "2-pyrazolin-5-one" refers to the group:

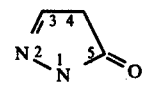

with the conventional numbering system shown above. Thus the term "1,3-dimethyl-4-chloro-4-(alpha-chloro-2',4'-dichlorobenzyl)-2-pyrazolin-5-one" refers to the group:

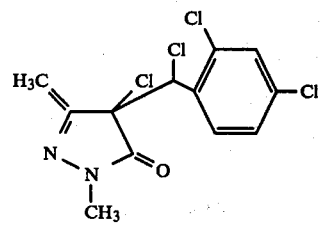

DETAILED DESCRIPTION OF THE INVENTION

The compounds of the present invention are prepared according to the following scheme:

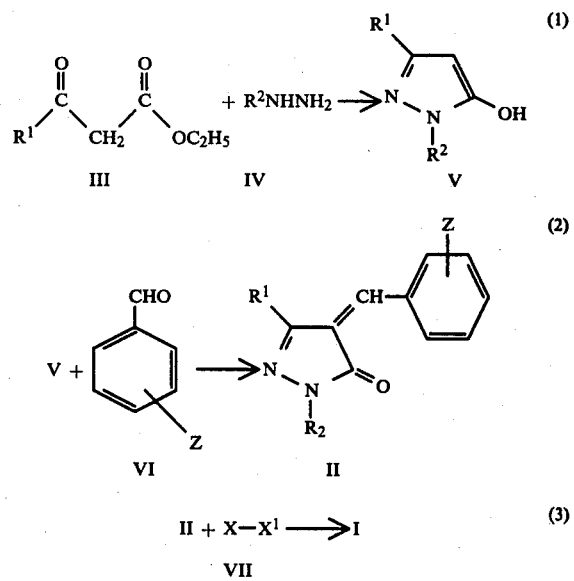

where $R^1$, $R^2$, $X^1$ and X are as defined above and Z represents potential substitution on the aromatic ring.

Reaction (1) is a conventional cyclization reaction. This reaction is described in Chem. Ber., 41, 555 (1908), which is incorporated herein by reference. Reaction (1) is conducted by adding an essentially equimolar amount of III to an alkylhydrazine, IV. The reaction is conducted in the liquid phase employing an organic solvent such as ethanol, methanol, chloroform and the like. Reaction pressure is not critical and for convenience the reaction is generally conducted at atmospheric pressure. The reaction is generally conducted at from 0°–100° C., although preferably at from 0° C. to room temperature and is generally complete from within 1 to 24 hours. The product, V, is then isolated by conventional procedures such as extraction, filtration, chromatography, crystallization, distillation or alternatively is used in reaction (2) without purification and/or isolation.

Reaction (2) is conducted by adding an essentially equimolar amount of a substituted benzaldehyde, VI, to the 1,3-disubstituted-2-pyrazolin-5-one, V. The reaction is conducted in the liquid phase using an inert organic solvent such as benzene, toluene, and the like. Preferably, a catalytic amount of a quaternary ammonium salt such as piperidinium acetate is used to facilitate reaction completion. The reaction is generally conducted at from room temperature to 110° C. Preferably, the reaction is heated and the water generated during the reaction is removed via a Dean-Stark trap. The reaction is continued until the amount of water collected in the Dean-Stark trap indicates reaction completion. Reaction pressure is not critical and for convenience the reaction is generally conducted at atmospheric pressure. The product, II, is then isolated by conventional procedures such as extraction, filtration, chromatography, distillation or alternatively is used in reaction (3) without purification and/or isolation.

Compounds of formula I are prepared by halogenating the olefin as shown in reaction (3). Reaction (3) is conducted by adding an essentially equimolar amount of a halogen or a mixed halogen, VII, to II to yield I. The reaction is conducted in the liquid phase employing an inert organic solvent such as methylene chloride, benzene, chloroform and the like. Preferably, a catalytic amount of a quaternary ammonium chloride salt such as tri-n-octylmethylammonium chloride is added to the system to facilitate reaction completion and enhance the overall yield. The reaction is generally conducted at from 0° to 100° C. and preferably at from 10° C. to 50° C. Reaction pressure is not critical and for convenience the reaction is generally conducted at atmospheric pressure. The reaction is generally complete from within 1 to 24 hours. The product, I, is isolated by conventional procedures such as extraction, filtration, chromatography, distillation, crystallization and the like.

UTILITY

The compounds of this invention are effective in controlling fungal infections. In particular, the compounds of the invention are effective in controlling plant fungal infections caused by Rice Blast (*Piricularia oryzae*). The compounds of the invention are also useful for controlling leaf blights caused by organisms such as *Alternaria solani conidia* and *Septoria apii*. The compounds of the present invention are useful for controlling fungi as measured by the mycelial inhibition test such as *Rhizoctonia solani, Aspergillus Niger* and *Botrytis Cinerea*. However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contained from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

A further understanding of the invention can be had in the following non-limiting Examples. Wherein, unless expressly stated to the contrary, all temperatures and temperature ranges refer to the centigrade system and the term "ambient" or "room temperature" refers to about 20° to 25° C. The term "percent" refers to weight percent and the term "mol" or "moles" refers to gram mols. The term equivalent refers to a quantity of reagent equal to mols, to the mols of the preceding or succeeding reagent recited in that example in terms of finite mols or finite weight or volume. Geometric isomer and racemic mixtures are used as starting materials and corresponding isomer mixtures are obtained as products.

Compounds prepared in accordance with Examples 1 to 3 below are listed in Table I.

EXAMPLE 1

Preparation of 1,3-dimethyl-2-Pyrazolin-5-one 46.1 gm of methyl hydrazine was added dropwise to a solution of 130 gm of ethyl acetoacetate in 150 ml of absolute ethanol under a reflux condenser. The reaction was strongly exothermic and was allowed to stir for four hours at room temperature. The ethanol was removed by stripping to give an orange solid. The product was recrystallized from methylene chloride-hexane to give 92 gm of 1,3-dimethyl-2-pyrazolin-5-one as a white solid, m.p. 113°–117° C.

EXAMPLE 2

Preparation of 1,3-dimethyl-4-(2',4'-dichlorobenzylidene)-2-Pyrazolin-5-one 13.8 gm of 1,3-dimethyl-2-pyrazolin-5-one and 21.5 gm of 2,4-dichlorobenzaldehyde was dissolved in toluene. The system was refluxed under a Dean-Stark condensor until 2.3 gm of water was collected. The reaction was stopped and the toluene removed by stripping. The product was recrystallized from toluene to give 27 gm of 1,3-dimethyl-4-(2',4'-dichlorobenzylidine)-2-pyrazolin-5-one as red crystals, m.p. 127.5°–128.5° C.

EXAMPLE 3

Preparation of 1,3-dimethyl 4-chloro-4-(alpha-chloro-2',4'-dichlorobenzyl)-2-Pyrazolin-5-one 5 gm of 1,3-dimethyl-4-(2',4'-dichlorobenzylidine)-2-pyrazolin-5-one was dissolved in 50 ml of dichloromethane. $Cl_2$ gas was then bubbled in. The system was stirred at room temperature until the required amount of $Cl_2$ was taken up. The methylene chloride was removed by stripping to give 7 gm of the crude product. The 1,3-dimethyl-4-chloro-4-(alpha-chloro-2',4'-dichlorobenzyl)-2-pyrazolin-5one was isolated by chromatography as a white solid, m.p. 113°–115° C. Listed as compound number 1 in Table I.

Other compounds which are prepared in accordance with Examples 1 to 4 include for instance:
1,3-dimethyl-4-bromo-4-(alpha-bromo-2',4'-dichlorobenzyl)-2-pyrazolin-5-one;
1,3-dimethyl-4-chloro-4-(alpha-chloro-2',4'-dibromobenzyl)-2-pyrazolin-5-one;
1,3-dimethyl-4-chloro-4-(alpha-chloro-2',4'-dimethylbenzyl)-2-pyrazolin-5-one;
1,3-dimethyl-4-chloro-4-[alpha-chloro-3',5'-di-(trifluoromethyl)benzyl]-2-pyrazolin-5-one;
1,3-dimethyl-4-chloro-4-(alpha-chloro-4'-t-butylbenzyl)-2-pyrazolin-5-one;
1,3-dimethyl-4-bromo-4-(alpha-chloro-2',4'-difluorobenzyl)-2-pyrazolin-5-one;
1,3-dimethyl-4-bromo-4-(alpha-bromo-2',4'-difluorobenzyl)-2-pyrazolin-5-one;
1,3-dimethyl-4-chloro-4-(alpha-chloro-2',4'-diiodobenzyl)-2-pyrazolin-5-one;
1,3-diethyl-4-chloro-4-(alpha-chloro-2',4'-dichlorobenzyl)-2-pyrazolin-5-one;
1-ethyl-3-methyl-4-chloro-4-(alpha-chloro-2',4'-dichlorobenzyl)-2-pyrazolin-5-one;
1-isopropyl-3-hexyl-4-bromo-4-(alpha-chloro-2',4'-dibromobenzyl)-2-pyrazolin-5-one;
1,3-dimethyl-4-chloro-4-(alpha-chloro-3'-trifluoromethylbenzyl)-2-pyrazolin-5-one;
1,3-dimethyl-4-chloro-4-(alpha-chloro-2'-nitrobenzyl)-2-pyrazolin-5-one;
1,3-dimethyl-4-chloro-4-(alpha-chloro-3'-nitrobenzyl)-2-pyrazolin-5-one;
1,3-dimethyl-4-chloro-4-(alpha-chloro-4'-nitrobenzyl)-2-pyrazolin-5-one.

EXAMPLE 4

Mycelial Inhibition

A number of the compounds of the present invention were evaluated for in-vitro fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C. and the data is taken after 24 hours. Fungicidal activities are measured by a zone of inhibited mycelial growth from the center of the paper strip. The effectiveness of the compounds tested for fungicidal activity is reported in Table IV for those compounds which were effective in inhibiting mycelial growth. The activity is reported in the terms of $$\frac{\text{micrograms/cm}^2 \text{ for 99\% control of the fungus for test compound}}{\text{micrograms/cm}^2 \text{ for 99\% control of the fungus for standard}} \times 100$$

EXAMPLE 5

Grape Downy Mildew Control

The compounds of the invention were tested for the control of the grape downy mildew organism *Plasmopara viticola*. Detached leaves, between 70 and 85 mm in diameter, of 7-week old *Vitis vinifera* cultivar Emperor grape seedlings were used as hosts. The leaves were sprayed with a 250 ppm solution of the test compound in acetone. The sprayed leaves were dried, inoculated with a spore suspension of the organism, placed in a humid environmental chamber and incubated at 66° to 68° F. and about 100% relative humidity. After incubation for two days, the plants were then held in a greenhouse seven to nine days; then the amount of disease control was determined. The percent disease control provided by a given test compound was based on the percent disease reduction relative to untreated check plants. The results are tabulated in Table II.

EXAMPLE 6

Tomato Early Blight

Compounds of the invention were tested for the control of the tomato early blight organism, *Alternaria solani conidia*. Tomato(variety Bonny Best) seedlings of 6 to 7 weeks old were used. The tomato plants were sprayed with a 250 ppm solution of the test compound in an acetone-and-water solution containing a small amount of a nonionic emulsifier. The sprayed plants were inoculated one day later with the organism, placed in the environmental chamber and incubated at 66° to 68° F. and 100% relative humidity for 24 hours. Following the incubation, the plants were maintained in a greenhouse for about 12 days. Percent disease control was based on the percent disease development on untreated check plants. The compounds tested and the results are tabulated in Table II.

EXAMLE 7

Celery Late Blight

The celery late blight tests were conducted using celery (Utah) plants 11 weeks old. The celery late blight organism was *Septoria apii*. The celery plants were sprayed with 250 ppm solutions of the candidate toxicant mixed with acetone, water and a nonionic emulsifier. The plants were then inoculated with the organism and placed in an environmental chamber and incubated at 66° to 68° F. in 100% relative humidity for an extended period of time (approximately 48 hours). Following the incubation the plants were allowed to dry and then were maintained in a greenhouse for approximately 14 days. The percent disease control provided by a given candidate toxicant is based on the percent disease reduction relative to untreated check plants. The results are reported in Table II.

EXAMPLE 8

Rice Blast

Compounds of this invention were tested for control of the rice blast organism, *Piricularia oryzae*, using 10 to 14-day old rice plant seedlings (Calrose M-9 variety). Seedling plants were sprayed with a 625 ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on untreated check plants:

$$\% \text{ Control} = 100 \times \left( \frac{\% \text{ disease in treated plants}}{\% \text{ disease in check}} \right)$$

the results are tabulated in Table III.

EXAMPLE 9

Bean Powdery Mildew

The compounds of the invention were tested for the control of the Bean Powdery Mildew organism *Erysiphe polygoni*. Seedling bean plants were sprayed with a 250 ppm solution of the test compound in acetone, water and a nonionic emulsifier. The sprayed plants were then inoculated 1 day later with the organism. The plants were maintained for 10 days at temperature of 68° F. at night with daytime temperatures of 72° to 80° F.; relative humidity was maintained at 40% to 60%. The percent disease control provided by a given test compound was based on the percent disease reduction relative to the untreated check plants. The results are tabulated in Table II.

EXAMPLE 10

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250 ppm suspension of the test compound in acetone, water and a nonionic emulsifier. The sprayed plants were then inoculated 1 day later with the organism, placed in an environmental chamber and incubated at 66° to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE 11

Leaf Rust

The Leaf Rust test was made using pinto beans. The pathogen was *Uromyces phaseoli tipica*. The pinto bean plants were sprayed with a 250 ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° to 70° F. The plants were then removed from the chamber, allowed to dry, and then maintained in a greenhouse at a 60% to 80% relative humidity. The rate of infection on the leaves was made after about 14 days. The percent disease control provided by a given test compound was based on the percent disease reduction relative to untreated check plants. The results are reported in Table II.

TABLE I

| COMPOUND NUMBER | COMPOUNDS OF THE FORMULA | ANALYSIS | | | | | | FORM | m.p. |
|---|---|---|---|---|---|---|---|---|---|
| | | Carbon Calc. | Fd. | Hydrogen Calc. | Fd. | Nitrogen Calc. | Fd. | | |
| 1 | 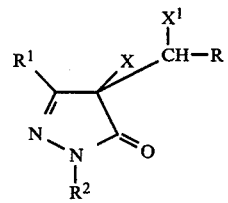 | 42.39 | 44.02 | 2.96 | 3.07 | 8.24 | 8.58 | white solid | 113–115° C. |

TABLE II

FUNGICIDAL ACTIVITY % CONTROL

| GDM | CLB | TEB | BR | BPM | TLB |
|---|---|---|---|---|---|
| — | 44 | 23 | 0 | 8 | 0 |

GDM - Grape Downy Mildew
CLB - Celery Lake Blight
TEB - Tomato Early Blight
BPM - Bean Powdery Mildew
BR - Bean Rust Eradicant
TLB - Tomato Late Blight

TABLE III

FUNGICIDAL ACTIVITY AGAINST RICE BLAST % CONTROL

| Compound No. | 625 ppm | 250 ppm | 100 ppm |
|---|---|---|---|
| 1 | 83 | 76 | 38 |

TABLE IV

MYCELIAL INHIBITION % STANDARD[1]

| | RHIZOC. | BOTRYTIS | ASPER. |
|---|---|---|---|
| 1 | 108 | 13 | 59 |

RHIZOC. - *Rhizoctonia Solani*
ASPER. - *Aspergillus Niger*
BOTRYTIS - *Botrytis Cinerea*
[1]STANDARD - DIFOLATAN ®

What is claimed is:

1. A compound of the formula $$\begin{array}{c} R^1 \diagdown \diagup X \diagdown \diagup CH-R \\ \phantom{R^1 \diagdown}  \phantom{X} \diagup X^1 \\ N \diagdown N \diagup \!\!=\!\! O \\ \phantom{N \diagdown} R^2 \end{array}$$

wherein R is phenyl or phenyl substituted with 1 to 3 substituents independently selected from fluoro, chloro, bromo, iodo, nitro, and trifluoromethyl; $R^1$ is lower alkyl; $R^2$ is lower alkyl; and X and $X^1$ are independently halogen.

2. A compound of the formula defined in claim 1 wherein R is 2,4-dihalophenyl.

3. A compound of the formula defined in claim 2 wherein R is 2,4-dichlorophenyl.

4. A compound of the formula defined in claim 3 wherein $R^1$ is methyl.

5. A compound of the formula defined in claim 4 wherein $R^2$ is methyl.

6. A compound of the formula defined in claim 5 wherein X and $X^1$ are chloro.

7. A method for controlling of fungi which comprises applying to the fungus or its habitat a fungicidally effective amount of the compound of the formula defined in claim 1.

8. A method for controlling of fungi which comprises applying to the fungus or its habitat a fungicidally effective amount of the compound of the formula defined in claim 6.

9. A method according to claim 7 wherein said fungus is Rice Blast.

10. A fungicidal composition comprising a biologically inert carrier and a fungicidally effective amount of the compound defined in claim 1.

11. A fungicidal composition comprising a biologically inert carrier and a fungicidally effective amount of the compound defined in claim 6.

* * * * *